(12) United States Patent
Bajaj et al.

(10) Patent No.: US 10,076,286 B1
(45) Date of Patent: Sep. 18, 2018

(54) METHODS AND DEVICES FOR CIRCADIAN RHYTHM MONITORING

(71) Applicant: Verily Life Sciences LLC, Mountain View, CA (US)

(72) Inventors: Vikram Singh Bajaj, Mountain View, CA (US); Sarel Kobus Jooste, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 839 days.

(21) Appl. No.: 14/519,825

(22) Filed: Oct. 21, 2014

(51) Int. Cl.
| | |
|---|---|
| A61B 5/00 | (2006.01) |
| A61B 5/0205 | (2006.01) |
| A61B 5/11 | (2006.01) |
| A61B 5/145 | (2006.01) |
| A61B 5/021 | (2006.01) |
| A61B 5/024 | (2006.01) |

(52) U.S. Cl.
CPC ........ *A61B 5/7275* (2013.01); *A61B 5/02055* (2013.01); *A61B 5/1118* (2013.01); *A61B 5/14542* (2013.01); *A61B 5/6802* (2013.01); *A61B 5/021* (2013.01); *A61B 5/024* (2013.01)

(58) Field of Classification Search
CPC .................................................. A61B 5/7275
USPC ....................................................... 600/301
See application file for complete search history.

(56) References Cited

U.S. PATENT DOCUMENTS

| | | | |
|---|---|---|---|
| 7,214,190 | B1 | 5/2007 | Wilson |
| 7,701,580 | B2 | 4/2010 | Bassler et al. |
| 7,763,856 | B2 | 7/2010 | Kiesel et al. |
| 7,817,254 | B2 | 10/2010 | Hegyi et al. |
| 7,817,276 | B2 | 10/2010 | Kiesel et al. |
| 7,844,314 | B2 | 11/2010 | Al-Ali |
| 7,894,068 | B2 | 2/2011 | Bassler et al. |
| 8,153,949 | B2 | 4/2012 | Kiesel et al. |
| 8,323,188 | B2 | 12/2012 | Tran |
| 8,344,731 | B2 | 1/2013 | Lee |
| 8,368,402 | B2 | 2/2013 | Lee et al. |

(Continued)

FOREIGN PATENT DOCUMENTS

WO 2013106700 A1 7/2013

OTHER PUBLICATIONS

Manuel Arruebo, Mónica Valladares, and África González-Fernández, Antibody-Conjugated Nanoparticles for Biomedical Applications, Journal of Nanomaterials, vol. 2009 (2009), Article ID 439389, 24 pages (available at http://dx.doi.org/10.1155/2009/439389).

(Continued)

*Primary Examiner* — John R Downey
(74) *Attorney, Agent, or Firm* — McDonnell Boehnen Hulbert & Berghoff LLP

(57) ABSTRACT

Methods for characterizing a circadian rhythm of a wearer of a wearable device are provided. In one example, physiometric measurements are obtained over a period of time by one or more sensors of a wearable device configured to be mounted to a body surface of a wearer. A circadian rhythm of the wearer, such as a sleeping, waking, eating or movement pattern, is characterized based on the physiometric measurements. Based on the identified circadian rhythm, one or more settings of the wearable device, such as a timing or frequency of obtaining physiometric measurements, may be adjusted.

20 Claims, 6 Drawing Sheets

(56) References Cited

U.S. PATENT DOCUMENTS

| | | | |
|---|---|---|---|
| 8,446,275 | B2 | 5/2013 | Utter |
| 8,468,115 | B2 | 6/2013 | Gartenberg |
| 2004/0259270 | A1 | 12/2004 | Wolf |
| 2005/0054907 | A1 | 3/2005 | Page et al. |
| 2005/0215868 | A1* | 9/2005 | Kenjou ................ A61B 5/0002 600/300 |
| 2007/0255122 | A1 | 11/2007 | Vol et al. |
| 2009/0105560 | A1* | 4/2009 | Solomon ............. A61B 5/0002 600/301 |
| 2010/0049010 | A1 | 2/2010 | Goldreich |
| 2011/0015495 | A1* | 1/2011 | Dothie ................. G06F 19/322 600/300 |
| 2011/0028803 | A1 | 2/2011 | Ollmar |
| 2011/0117028 | A1 | 5/2011 | Zharov |
| 2011/0144528 | A1* | 6/2011 | Gurley ..................... A61B 5/01 600/549 |
| 2012/0303099 | A1* | 11/2012 | D'Ambrosio ........ A61N 5/0618 607/90 |
| 2013/0085399 | A1* | 4/2013 | Bennett ................ A61B 5/0215 600/483 |
| 2013/0197076 | A1* | 8/2013 | Dressman ............ A61K 31/343 514/469 |
| 2016/0029898 | A1* | 2/2016 | LeBoeuf ............. A61B 5/0205 600/301 |

OTHER PUBLICATIONS

Shao et al, "Magnetic nanoparticles for biomedical NMR-based diagnostics," Beilstein Journal of Nanotechnology, 2010, 1, 142-154.

Liu et al, "Magnetic resonance monitoring of focused ultrasound/magnetic nanoparticle targeting delivery of therapeutic agents to the brain," PNAS Early Edition, 2010, pp. 1-6.

* cited by examiner

METHODS AND DEVICES FOR CIRCADIAN RHYTHM MONITORING

BACKGROUND

Unless otherwise indicated herein, the materials described in this section are not prior art to the claims in this application and are not admitted to be prior art by inclusion in this section.

A number of scientific methods have been developed in the medical field to evaluate a person's health state. A person's health state may, for example, be evaluated based on the measurement of one or more physiometric parameters, such as pulse, oxygen saturation ($SpO_2$), and blood pressure. In a typical scenario, these measurements may be taken in the home or a health-care setting by using several discrete devices or sensors and, in some cases, by drawing blood or other bodily fluid. For most people, the measurements or blood tests are performed infrequently, and changes in a physiometric parameter, which may be relevant to health state, may not be identified, if at all, until the next measurement is performed.

Monitoring of an individual's circadian cycle may also be important to evaluating health state. The timing of many molecular, behavioral, mental and physical functions is governed by one or more circadian rhythms. Circadian rhythms can be used in the diagnosis sleep disorders, intervene on abnormal sleep patterns, time the delivery of therapeutic agents, optimize activity and performance, and modify behavior. Indications of the circadian cycle may include an individual's sleep/wake, appetite, thirst, excretion, core body temperature and physical activity cycles.

The timing of a mammal's circadian rhythm is typically measured by phase markers such as melatonin secretion, core body temperature and plasma level of cortisol. At present, these markers are measured infrequently, for example, when an individual visits a physician or laboratory, or at certain points throughout the day. Further, cortisol level and melatonin secretion are generally measured by invasive procedures, such as a blood draw. Other modes of gathering information regarding an individual's circadian cycle, such as actigraphy and questionnaires can suffer from a lack of sensitivity and reliability.

SUMMARY

A wearable device may collect physiometric data from a wearer of the device and transmit that data to the cloud or other remote server or device. The physiometric data may be analyzed to characterize one or more circadian rhythms of the wearer. In an initial state, the server may analyze the physiometric data by, in some examples, identifying one or more cyclical patterns, to determine whether the collected data is sufficient to characterize a circadian rhythm of the wearer. The server may determine, based on the analysis of the data, one or more instructions for transmission to the wearable device. In cases where the initial data is determined to be insufficient, the server may instruct the wearable device to collect additional data comprising one or more additional physiometric measurements over an additional period of time. This system of feedback may continue until the server determines that the type of data and manner in which the wearable device collects data is sufficient to characterize one or more circadian rhythms of the wearer. A wearer's characterized circadian rhythms may be used to determine a health state of the wearer and, in some examples, to provide recommendations to a wearer.

Some embodiments of the present disclosure provide a method including: (1) receiving, at a server, initial data from a wearable device, wherein the initial data comprises one or more initial physiometric measurements obtained by an initial set of one or more sensors of the wearable device over an initial period of time, wherein the wearable device is configured to be mounted to a body surface of a wearer; (2) performing, by the server, an analysis of the initial data to determine whether the initial data is sufficient to characterize a circadian rhythm of the wearer; (3) determining, by the server, one or more instructions, based on the analysis of the initial data; and (4) transmitting, by the server, the one or more instructions to the wearable device.

Further embodiments of the present disclosure provide a method including: (1) obtaining, via one or more sensors of a wearable device, one or more physiometric measurements over a period of time, wherein the wearable device is configured to be mounted to a body surface of a wearer; (2) characterizing a circadian rhythm of the wearer based on the one or more physiometric measurements; and (3) adjusting one or more settings of the wearable device based on the circadian rhythm of the wearer.

Still further embodiments of the present disclosure provide a wearable device including: (1) a mount configured to mount the wearable device to a body surface; (2) one or more sensors, wherein the one or more sensors are configured to obtain one or more physiometric measurements; and (3) a controller, wherein the controller is configured to control the one or more sensors such that the one or more physiometric measurements obtained by the one or more sensors are sufficient to characterize a circadian rhythm.

These as well as other aspects, advantages, and alternatives, will become apparent to those of ordinary skill in the art by reading the following detailed description, with reference where appropriate to the accompanying drawings.

DETAILED DESCRIPTION

Figure 1:
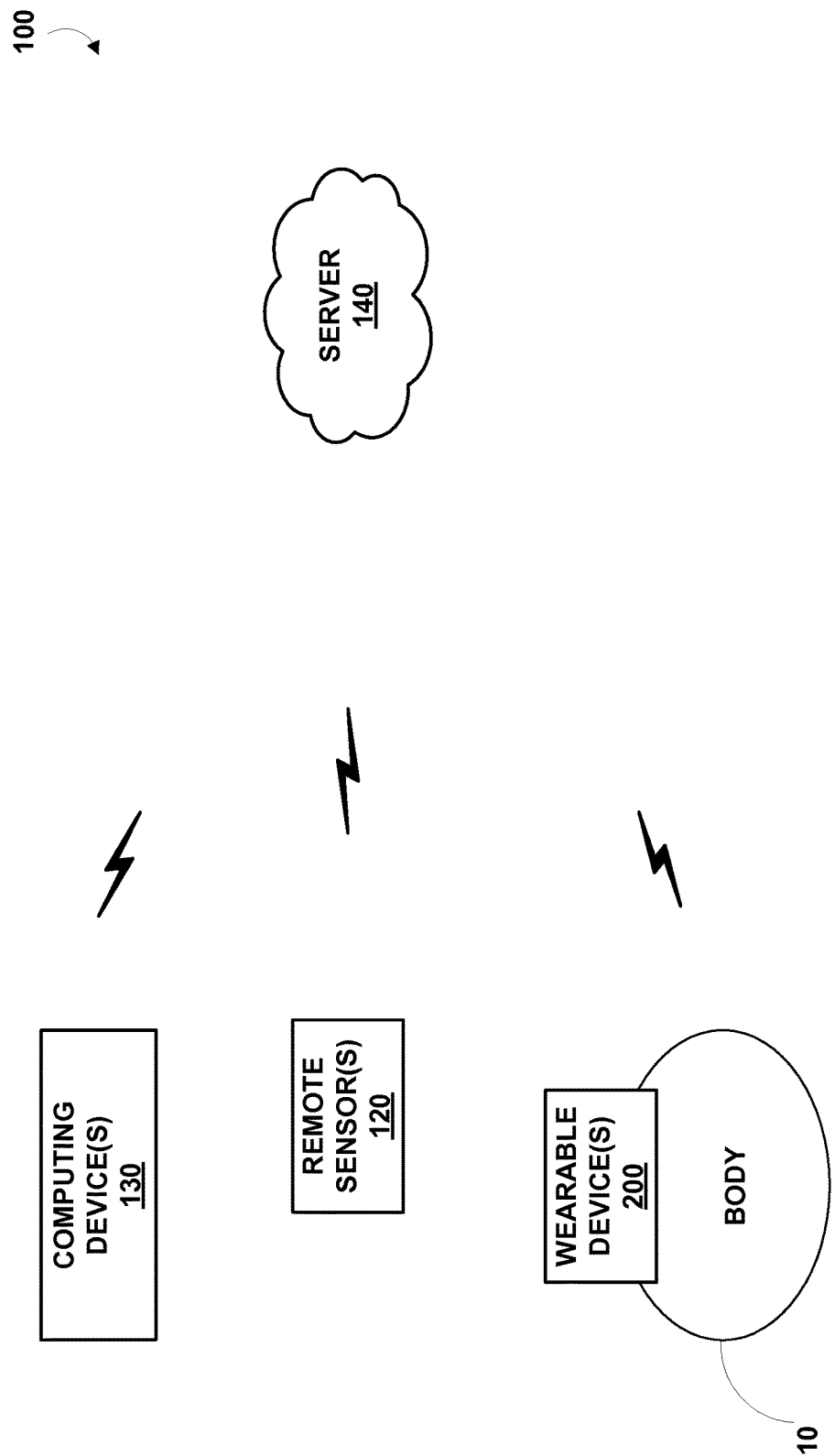
FIG. 1 is a block diagram of an example system that includes a wearable device, according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Physiometric correlates of an individual's circadian rhythms may be monitored using one or more wearable devices. A circadian rhythm generally refers to any physiological, mental, physical, or behavioral variation or rhythm with a cycle of approximately 24 hours. For the purpose of this disclosure, the terms "circadian rhythm" or "circadian cycle" shall also include any variation or rhythm with a cycle of less than or greater than 24 hours, such as diurnal, infradian, and ultradian rhythms. Circadian rhythms can coordinate or influence the timing of biological functions, including sleep, activity, appetite, thirst, waste excretion, hormone release, cell regeneration and body temperature. Accordingly, health, safety, performance and productivity can be affected by circadian rhythms and disruptions thereto. Numerous health problems, including some forms of depression, as well as many sleep, neurological, cardiovascular and endocrine disorders, have been associated with circadian rhythm dysfunctions. In addition, circadian rhythms may influence the effectiveness of certain drugs and, therefore, may be important to the timing of drug delivery.

A wearable device may monitor generalized analogues of an individual's vital signs by collecting various forms of physiometric data, including blood flow, body or skin temperature, skin color, perspiration, body movement, eye movement, sound, and other measurements. This data may be collected by sensors such as accelerometers, IMUs, proximity sensors, microphones, gyroscopes, magnetometers, barometers, thermometers, optical/multispectral sensors, ultrasonic sensors, Doppler sensors, galvanic skin response (GSR) instruments, odometers, and pedometers and transmitted to the cloud or other remote server or remote computing device. Molecular sensors may also be used to measure the levels of melatonin or other small molecules, metabolites, hormones, peptides, or proteins present in blood, saliva, tear fluid, or other body fluid that are involved with or correlated with the circadian cycle. These molecular sensors may be integrated as part of or be provided separate from the wearable device(s). Additionally, the wearable device may collect certain contextual data that may be related to or have an effect on the circadian cycle, such as an individual's location, altitude, and travel history, time of day, and ambient temperature, light, sound, pressure and humidity, and allergen and pollution levels. Accordingly, the wearable device may include, or be in communication with, a location-tracking sensor (e.g., a GPS device), a light intensity sensor, a thermometer, a barometer, a microphone and a clock. An individual's personal or demographic data, such as sex, race, region or country of origin, age, weight, height, employment, medical history, etc., may also be collected and transmitted to the cloud.

The term "wearable device," as used in this disclosure, refers to any device that is capable of being worn or mounted at, on, in or in proximity to a body surface, such as a wrist, ankle, waist, chest, ear, eye, head or other body part. As such, the wearable device can collect data while in contact with or proximate to the body. For example, the wearable device can be configured to be part of a contact lens, a wristwatch, a head-mountable device, an orally-mountable device such as a retainer or orthodontic braces, a headband, a pair of eyeglasses, jewelry (e.g., earrings, ring, bracelet), a head cover such as a hat or cap, a belt, an earpiece, other clothing (e.g., a scarf), and/or other devices. Further, the wearable device may be mounted directly to a portion of the body with an adhesive substrate, for example, in the form of a patch, or may be implanted in the body, such as in the skin or another organ.

In some examples, the data described above may be collected directly by sensors integrated on the wearable device. Alternatively, or additionally, some or all of the data described above may be collected by sensors placed on other portions of a wearer's body or in communication with the body, other computing devices remote to the wearable device (such as a remote device having location tracking and internet capabilities, e.g. a smartphone, tablet or head-mountable device), or by manual input by the wearer. For example, the wearer may manually input when she is eating, sleeping, exercising, or travelling, among other things. Data may also be collected from applications on other computing devices linked with the wearable device such as an electronic calendar, social media applications, restaurant reservation applications, travel applications, etc.

The data collected by the wearable device can be processed in an unadulterated (raw) form, pre-processed, filtered or reduced by, for example, apodization, or fit using mathematical models and heuristics to reveal familiar physiometric parameters including pulse, oxygen saturation ($SpO_2$), and blood pressure. Any of these parameters can be inputs to algorithms for identifying characteristic oscillatory cycles.

In an initial stage, the wearable device may be calibrated over time to find an appropriate signal indicative of an individual's circadian cycle. This calibration stage may last weeks, months or up to a year. During this stage, the wearable device may communicate with a remote server or cloud computing device to determine whether the metrics being monitored by the device are sufficient or appropriate for providing an indication of circadian rhythms. For example, the cloud computing device may process data collected by the wearable device and determine that the collected data is not sufficient to identify one or more circadian rhythms. Accordingly, the cloud computing device may direct the wearable device to collect different data (i.e., look for different things), or collect data differently (i.e., collect at a different frequency, on different days of the week, or at different times of day). The calibration period may last until the cloud computing device has reached equilibrium and has determined that the wearable device is collecting the right kind of data and in the right way, to provide information on the wearer's circadian rhythms.

Processed data collected from the wearable devices may be used in a number of applications. For example, collected data may be used to monitor circadian rhythms and diagnose circadian sleep disorders. Sensor outputs from the wearable device(s) may be combined using algorithms for spectral or harmonic analysis. Circadian rhythms and their perturbations may be identified from the processed data and assigned to diagnostic categories, such as one of the six ICSD-2 classifications of sleep disorders.

The circadian cycle may be reset or modulated using one of several interventions, including light exposure or the administration of melatonin. Data collected from the wearable device can be used to time these interventions, calibrate the dosage (initially and dynamically), and monitor treatment response. The device can serve as a companion diagnostic.

In another example, the collected data may be used to time the delivery of therapeutic agents. The pharmacokinetics and pharmacodynamics of some systemic and local therapies can be sensitive to circadian cycles. Timing the phase of therapeutic administration may increase their effectiveness, decrease dose, or reduce side effects. The wearable device can serve as a companion diagnostic.

Circadian cycle can also affect an individual's performance in standardized tests of physical and cognitive ability, as well as in athletic or cognitive tasks. Data collected from the wearable device can be used to optimize the time at which these tasks are attempted, or to standardize the time within the circadian cycle at which clinical instruments are administered as a mechanism of experimental control.

Further, some activities, such as driving a car, operating machinery, flying an airplane, or performing surgery can be dangerous if attempted during periods of circadian disregulation. The device output can be used to warn its wearer of related dangers.

Data collected from the wearable device may also be used for behavior modification. In one example, sleep-related behaviors may be modified in order to yield restful sleep. In addition, other psychological behaviors and the effectiveness of behavior modification interventions are also modulated by circadian cycles. Accordingly, output from the wearable device may be used to time behavior modification interventions according to the circadian cycle.

The wearable device may be used to monitor circadian patterns and identify circadian dysregulation. Circadian dysregulation, either in relative (individual) or population-normalized terms, can be associated with the acute worsening of many chronic diseases or the acute emergence of new disease states, such as sudden cardiac death.

Changes in circadian rhythms and their general phase coherence have, in some examples, been associated with generalized morbidity and mortality independent of precise aetiology. The historical record produced by the wearable device can therefore be used as a general health assay. Further, dynamic phenomena in the phase trajectories, including critical slowing down and other derived metrics, may be prognostic of a phase transition from health to disease (e.g. in depression).

The term or "health state" as used herein should be understood broadly to include any state of wellness, disease, illness, disorder, or injury, any condition or impairment—e.g., physiologic, psychological, cardiac, vascular, orthopedic, visual, speech, or hearing—or any situation affecting the health of an individual.

It should be understood that the above embodiments, and other embodiments described herein, are provided for explanatory purposes, and are not intended to be limiting.

II. Example Wearable Devices and Systems

As shown in FIG. 1, a system 100 may include one or more wearable devices 200 configured to be mounted to or worn on, in or in proximity to a body 10, one or more remote sensors 120, and one or more computing devices 130 all in communication with a server 140. Remote sensor 120 may be any sensor not provided directly on the wearable device 200. For example, a remote sensor 120 may be mounted to an individual's bicycle or car, in an individual's kitchen or bathroom, near an individual's bed or outside of an individual's home. Computing device 130 may be any device having computing or internet capabilities, including a smartphone or tablet, a personal computer, a mobile or cellular telephone, or a web-based application. In one embodiment, the wearable device 200, remote sensor 120 and computing device 130 may all directly communicate with the server 140. In other embodiments (not shown), the one or more remote sensors 120 and wearable devices 200 indirectly communicate with server 140 via computing device 130.

The device 200, remote sensor 120 and/or computing device 130 may be capable of collecting, detecting or measuring a plurality of parameters from or associated with a person wearing the device, such as physiometric, contextual, and demographic parameters. As will be described further below, these parameters may be detected on one or more of the wearable device 200, the remote sensors 120 and the computing devices 130. Physiometric parameters may include blood flow, skin temperature, skin color, perspiration, body movement, eye movement, sound, analyte concentration, and other measurements.

Contextual parameters, such as an individual's location, altitude, and travel history, time of day, and ambient temperature, light, sound, pressure and humidity, and allergen and pollution levels. An individual's "location" could be any location with respect to a 2-dimensional or 3-dimensional coordinate system (e.g., a location with respect to X, Y and Z axes) or with respect to a cartographic location description (e.g., a street address), and may further include a global position (e.g., latitude, longitude and elevation), a hyper-local position (such as a location within a home or building), and/or any position at any level of resolution therebetween. Demographic parameters may include sex, race, region or country of origin, age, weight, height, employment, occupation, and medical history, etc.

The wearable device 200, remote sensor(s) 120 and computing device(s) 130 may be configured to transmit data, such as collected physiometric, contextual and personal parameter data via a communication interface over one or more communication networks to the remote server 140. The communication interface may include any means for the transfer of data, including both wired and wireless communications, such as a universal serial bus (USB) interface, a secure digital (SD) card interface, a plain old telephone service (POTS) network, a cellular network, a fiber network and a data network. In one embodiment, the communication interface includes a wireless transceiver for sending and receiving communications to and from the server. The wearable device 200, remote sensor(s) 120 and computing device(s) 130 may also be configured to communicate with one another via any communication means.

Further, the computing device 130 may be capable of accessing physiometric, contextual and demographic data of an individual on the internet, the individual's electronic calendar, or from a software application. The computing device 130 may collect data regarding the individual's schedule, appointments, and planned travel. In some cases, the computing device 130 may also access the internet or other software applications, such as those operating on an individual's smartphone. For example, the computing device 130 may access an application to determine the temperature, weather and environmental conditions at the individual's location. All of this collected data may be transmitted to the remote server 140.

In addition to receiving data from the wearable device 200, remote sensor(s) 120 and computing device(s) 130, the server may also be configured to gather and/or receive additional physiometric, contextual and demographic data from other sources. For example, the server may be configured to regularly receive viral illness or food poisoning outbreak data from the Centers for Disease Control (CDC) and weather, pollution and allergen data from the National Weather Service. Further, the server may be configured to receive data regarding an individual's health state or existing medical conditions from a hospital or physician. Such information may be used in the server's decision-making process, such as recognizing correlations and in generating recommendations.

One or more of the wearable device 200, remote sensor 120 or computing device 130 may also be capable of receiving an input from an individual and transmitting that input to the server 140. For example, the individual may input data relevant to her circadian cycle including the time she went to sleep, awoke from sleep, ate, exercised, went to the bathroom, etc. As will be described further below, the wearable device 200 may include an interface 280 with one or more controls 284 via which the wearer may provide an input. An individual may also provide an input on a computing device 130, such as a smartphone, tablet or laptop computer.

Figure 2:
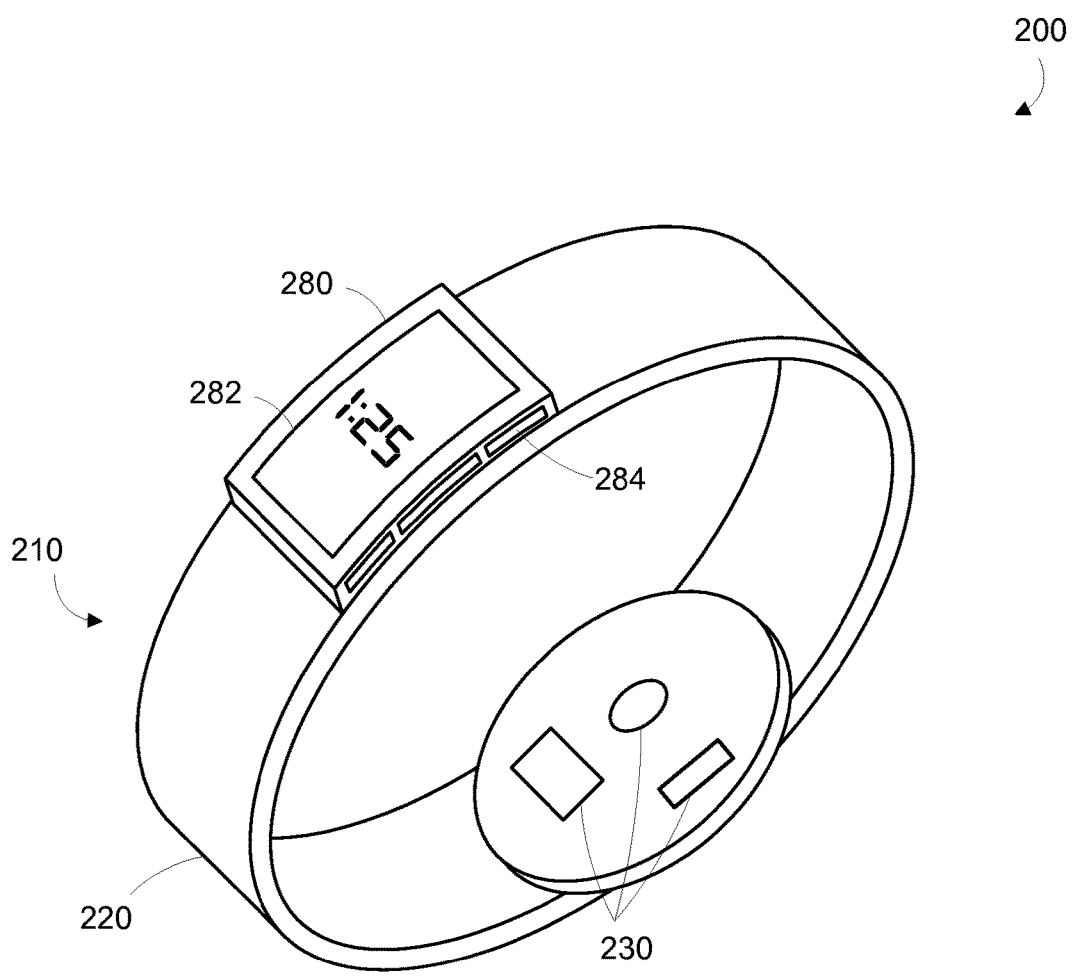
FIG. 2 illustrates an example of a wearable device.

Turning to FIG. 2, the wearable device 200 may be provided as any device configured to be mounted in, on or adjacent to a body surface. In the example shown in FIG. 2, the wearable device 200 is a wrist-mountable device 210, but many other forms are contemplated. The device may be placed in close proximity to the skin or tissue, but need not be touching or in intimate contact therewith. A mount 220, such as a belt, wristband, ankle band, necklace, or adhesive substrate, etc. can be provided to mount the device at, on or in proximity to the body surface. One or more wearable devices 200, each of which may be different (e.g., have different sensors), may be worn by an individual.

Figure 3:
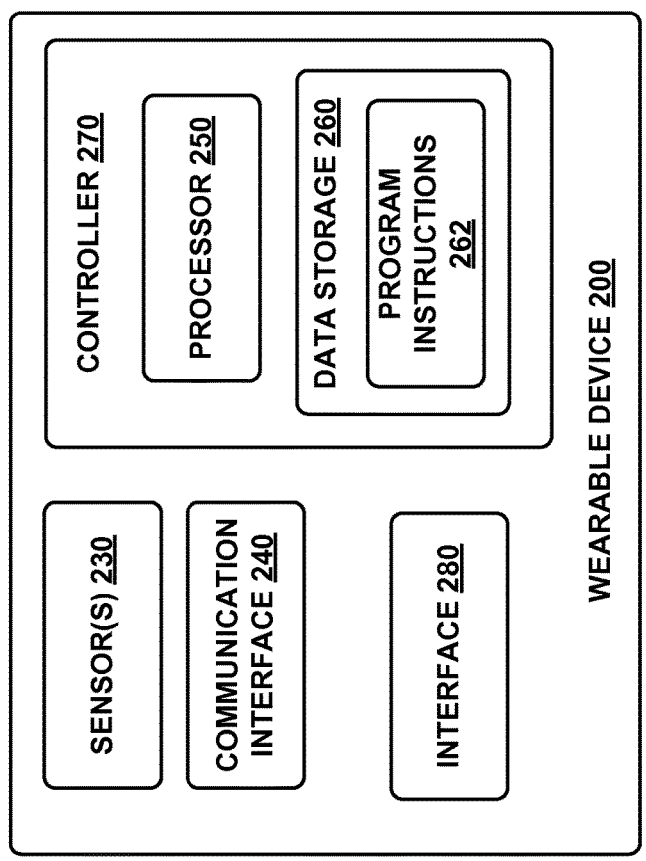
FIG. 3 is a schematic diagram of an example wearable device.

A schematic diagram of a wearable device 200, such as wrist-mountable device 210, is shown in FIG. 3. The wearable device 200 may include one or more sensors 230 for collecting data from or associated with a wearer of the device, a communication interface 240 for communicating collected data to a remote server or device, a controller 270, which may include a processor 250 and a data storage 260, and an interface 280. Communication interface 240 may include a wireless transceiver with an antenna that is capable of sending and receiving information to and from a remote source, such as a server 140.

The sensors 230 may include any device for collecting, detecting or measuring one or more physiometric, contextual or demographic parameters. Sensors for detecting and measuring physiometric parameters may include, but are not limited to, optical (e.g., CMOS, CCD, photodiode), multi-spectral, acoustic (e.g., piezoelectric, piezoceramic), Doppler, electrochemical (voltage, impedance), resistive, thermal, mechanical (e.g., pressure, strain), magnetic, or electromagnetic (e.g., magnetic resonance) sensors. In particular, the wearable device may include one or more accelerometers, IMUs, and gyroscopes for detecting movement, microphones for detecting speech and ambient noise, thermometers for detecting body and ambient temperatures, proximity sensors for detecting mechanical pressure, barometers for measuring atmospheric pressure, galvanic skin response (GSR) instruments for detecting perspiration and measuring skin resistance, and optical/multispectral sensors for sensing blood pressure, etc.

Some physiometric data may also be obtained using one or more molecular sensors for detecting and/or measuring one or more analytes present in blood, saliva, tear fluid, or other body fluid of the wearer of the device. The one or more analytes could include enzymes, reagents, hormones, proteins, viruses, bacteria, cells or other molecules, such as carbohydrates, e.g., glucose. In particular, one or more molecules, metabolites, hormones, peptides or proteins involved with or correlated with the circadian cycle, such as melatonin may be detected. Analyte detection and measurement may be enabled through several possible mechanisms, including electrochemical reactions, change in impedance, voltage, or current etc. across a working electrode, and/or interaction with a targeted bioreceptor. For example, analytes in a body fluid may be detected or measured with one or more electrochemical sensors configured to cause an analyte to undergo an electrochemical reaction (e.g., a reduction and/or oxidation reaction) at a working electrode, one or more biosensors configured to detect an interaction of the target analyte with a bioreceptor sensitive to that analyte (such as proteins, enzymes, reagents, nucleic acids, phages, lectins, antibodies, aptamers, etc.), and one or more impedimetric biosensors configured to measure analyte concentrations at the surface of an electrode sensor by measuring change in impedance across the electrode, etc. Other detection and quantification systems, including non-invasive detection mechanisms, such as optical and acoustic sensors, are contemplated. These molecular sensors may be integrated as part of or be provided separate from the wearable device(s).

Contextual parameters may be detected from, for example, a location-tracking sensor (e.g., a GPS or other positioning device), a light intensity sensor, a thermometer, a microphone and a clock. These sensors and their components may be miniaturized so that the wearable device may be worn on the body without significantly interfering with the wearer's usual activities. Additionally or alternatively, these sensors may be provided on or as part of a remote sensor 120 or a computing device 130.

Controller 270 is configured to control the one or more sensors 230 on the wearable device 200 based, at least in part, on instructions generated by the server 140 or other remote device. The instructions may be received by the controller 270 via the communication interface 240, which may be provided as a wireless transceiver. As will be explained further below, the instructions received by the wearable device 200 may be to adjust one or more settings of the sensors 230 such that the one or more physiometric measurements obtained by the one or more sensors are sufficient to characterize a circadian rhythm. For example, the controller 270 may control various settings of the wearable device 200, including the time(s) of day at which the one or more sensors 230 collect data from the wearer of the device 200 and the frequency at which the one or more sensors 230 collect data. The controller 270 may also adjust the type(s) of data collected by the wearable device by, for example, adjusting which sensors 230 collect data. Additionally or alternatively, the instructions may be for the controller 270 to provide one or more alerts or recommendations to the wearer via the interface 280. For example, the controller 270 may receive instructions to alert the wearer via the interface 280 that she has entered a stage of her circadian cycle when it may not be safe to operate a vehicle.

Processor 250 and data storage 260 may be provided as part of the controller 270. Example processor(s) 250 include, but are not limited to, CPUs, Graphics Processing Units (GPUs), digital signal processors (DSPs), application specific integrated circuits (ASICs). Data storage 260 is a non-transitory computer-readable medium that can include, without limitation, magnetic disks, optical disks, organic memory, and/or any other volatile (e.g. RAM) or non-volatile (e.g. ROM) storage system readable by the processor 250. The data storage 260 can include a data storage to store indications of data, such as sensor readings, program settings (e.g., to adjust behavior of the wearable device 200), user inputs (e.g., from a user interface on the device 200 or communicated from a remote device), etc. The data storage 260 can also include program instructions 262 for execution by the processor 250 to cause the device 200 to perform operations specified by the instructions. The operations could include any of the methods described herein. For example, the program instructions 262 may specify the timing and frequency of data acquisition by the sensors 230.

Further, the processor 250 itself may be configured to process the physiometric measurement data obtained by the sensors 230 to generate one or more instructions, such as program instructions 262, for controlling the sensor settings. In such cases, the instructions for adjusting one or more settings of the sensors 230 may be generated on the wearable device 200, in alternative or in addition to receiving instructions from the server or other remote processing device.

The wearable device 200 may also include an interface 280 via which the wearer of the device may receive one or more recommendations or alerts generated either from a remote server 140, remote computing device 130, or from the processor 250 provided on the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, as shown in FIG. 2, the interface 280 may include a display 282 where a visual indication of the alert or recommendation may be displayed. The display 282 may further be configured to provide an indication of the detected or collected physiometric, motion, contextual or personal parameters, for instance, the wearer's heart rate. In embodiments where the wearable device is not capable of supporting an interface 280, alerts and recommendations may be provided to the wearer on computing device 130. The interface 280 may also include one or more controls 284 via which a user may input an indication of her state, or, in some cases a rule related to the data detected by the wearable device. The controls 284 may allow a user to input or select one or more options regarding, for example, times and quality of sleep, times and type of exercise, times and content of meals, etc. These options may be displayed on the interface 280, for example, in lists or menus that the user may navigate using the controls 284. These inputs by the user may be transmitted to the server 140.

In other examples, the wearable device 200 may be provided as or include an eye-mountable device, a head mountable device (HMD) or an orally-mountable device. An eye-mountable device may, in some examples, take the form of a vision correction and/or cosmetic contact lens, having a concave surface suitable to fit over a corneal surface of an eye and an opposing convex surface that does not interfere with eyelid motion while the device is mounted to the eye. The eye-mountable device may include at least one sensor provided on a surface of or embedded in the lens material for collecting data. In one example, the sensor can be an amperometric electrochemical sensor for sensing one or more analytes present in tear fluid.

An HMD may generally be any display device that is capable of being worn on the head and places a display in front of one or both eyes of the wearer. Such displays may occupy a wearer's entire field of view, or occupy only a portion of a wearer's field of view. Further, head-mounted displays may vary in size, taking a smaller form such as a glasses-style display or a larger form such as a helmet or eyeglasses, for example. The HMD may include one or more sensors positioned thereon that may contact or be in close proximity to the body of the wearer. The sensor may include a gyroscope, an accelerometer, a magnetometer, a light sensor, an infrared sensor, and/or a microphone for collecting data from or associated with a wearer. Other sensing devices may be included in addition or in the alternative to the sensors that are specifically identified herein.

An orally mountable device may be any device that is capable of being mounted, affixed, implanted or otherwise worn in the mouth, such as on, in or in proximity to a tooth, the tongue, a cheek, the palate, the lips, the upper or lower jaw, the gums, or other surface in the mouth. For example, the device 200 can be realized in a plurality of forms including, but not limited to, a crown, a retainer, dentures, orthodontic braces, dental implant, intra-tooth device, veneer, intradental device, mucosal implant, sublingual implant, gingivae implant, frenulum implant, or the like. The orally-mountable device may include one or more sensors to detect and/or measure analyte concentrations in substances in the mouth, including food, drink and saliva. Sensor(s) that measure light, temperature, blood pressure, pulse rate, respiration rate, air flow, and/or physiometric parameters other than analyte concentration(s) can also be included.

One or more of the above-described types of wearable devices may be worn in combination to collect various types of physiometric, contextual and demographic data. Data collected from one or more wearable devices may be time-stamped to allow for correlation of data collected from each device.

III. Example Methods

Figure 4:
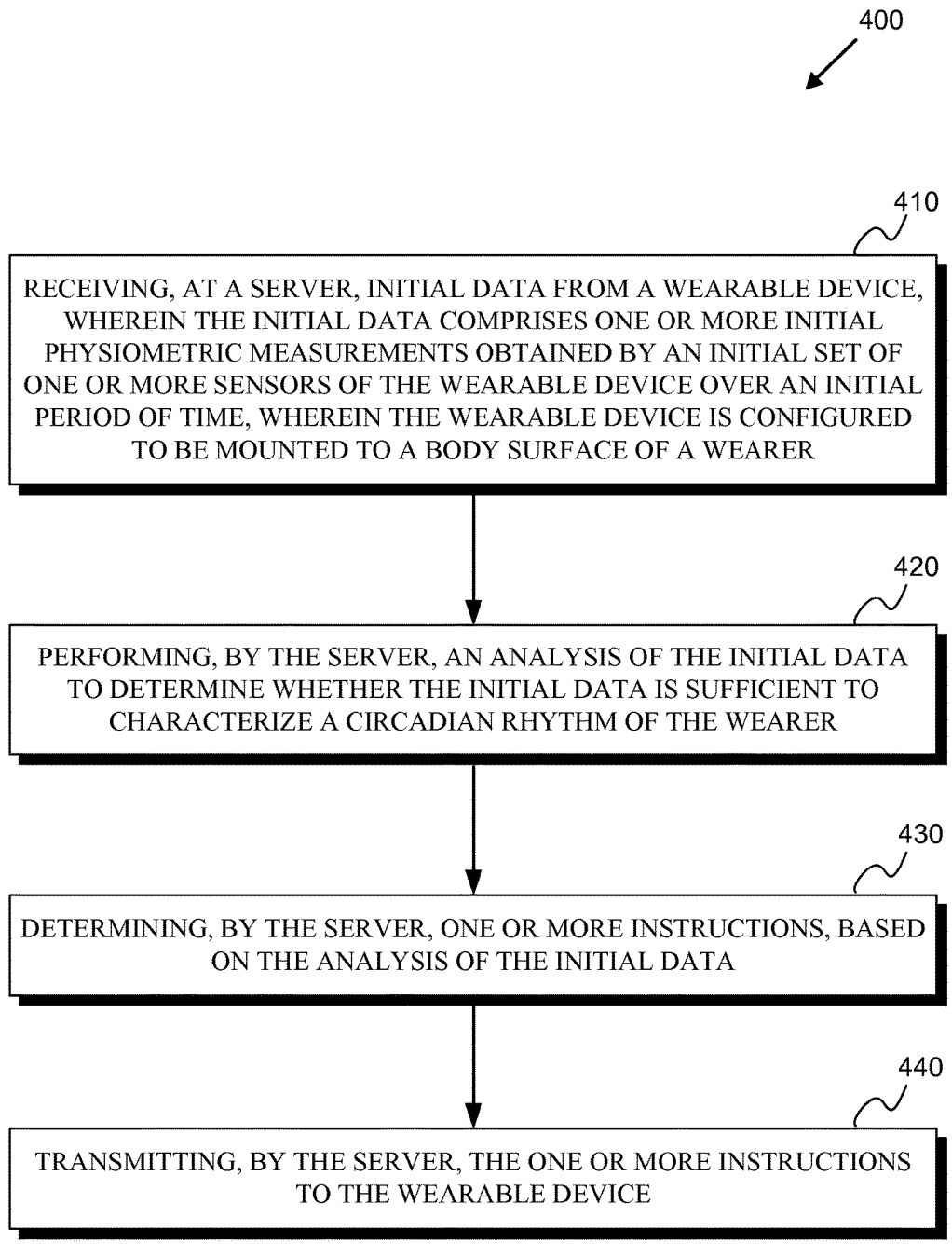
FIG. 4 is a flow chart of an example method, according to an example embodiment.

FIG. 4 is a flowchart of an example method 400 for monitoring one or more circadian rhythms with a wearable device. As described above, a wearable device 200, configured to be mounted to a body surface, may detect physiometric data from a wearer of the device. Initial data comprising one or more initial physiometric measurements, such as measurements of body motions, measurements of pulse, measurements of blood oxygen saturation, measurements of blood pressure, or measurements of body temperature, obtained by a wearable device is received by, for example, a remote server 140, such as a cloud computing network (410). The initial physiometric measurements are obtained by an initial set of one or more sensors of the wearable device over an initial period of time. In some examples, the initial period of time may be at least twenty-four hours, but may also be a period of several days, weeks or months or a year or more. The one or more sensors may include any of the types of sensors described above. The wearable device is configured to be mounted to a body surface and may be provided as any of the wearable devices 200 described above, including wrist-mountable device 210. While embodiments of the foregoing methods are described herein as being carried out on the server 140, it is contemplated that the methods may be carried out by a processor on the wearable device 200, remote sensor 120 or computing device 130.

The server performs an analysis of the initial data to determine whether the initial data is sufficient to characterize a circadian rhythm of the wearer (420). Based on its analysis of the initial data, the server determines one or more instructions (430) and transmits the instructions to the wearable device (440). In determining whether the initial data is sufficient to characterize a circadian rhythm of the wearer, the server may identify at least one cyclical pattern in the initial data. For example, after analyzing the initial data, the server may identify a pattern the way the wearer's skin temperature or respiration rate changes over the course of a day. The initial data may, for example, have been collected over the period of a week. Based on the at least one identified cyclical pattern, the server may further recognize one or more indications of the circadian rhythm of the wearer, such as sleeping, waking, eating, excretion and physical activity. The server may, for example, determine based on the cyclical pattern in the wearer's skin temperature and respiration rate when the wearer falls asleep and awakes.

The one or more instructions determined by the server may be based on the one or more indications of the wearer's circadian rhythm. For example, the server may instruct the wearable device to continue to collect data in the same manner. Additionally or alternatively, the server may analyze the identified indication of circadian rhythm to determine that the rhythm is abnormal or that the circadian rhythm has changed significantly from a previously-determined rhythm of the wearer. In this example, the server may instruct the server to collect additional data or different data over an additional period of time in order to determine the cause of the abnormal or changed circadian rhythm. In another example, upon determining an indication of circadian rhythm, the server may instruct the wearable device to provide an alert to the wearer of the device to modify a certain behavior or to administer a therapeutic agent at a certain time, based on the determined circadian rhythm.

The server may, on the other hand, analyze the initial data and determine that the initial data is insufficient to characterize the circadian rhythm of the wearer. In this respect, this analysis of the initial data can serve to calibrate the wearable device and the server to determine whether the metrics being monitored by the device are sufficient or appropriate for providing an indication of circadian rhythms of the wearer. In particular, the server may evaluate the data collected by the wearable device to determine the type, timing and frequency of data that the wearable device must collect in order to provide information on the wearer's circadian rhythms. Therefore, the one or more instructions determined by the server may be configured to cause the wearable device to collect additional data comprising one or more additional physiometric measurements over an additional period of time. The one or more instructions may further be configured to cause the wearable device to collect the one or more additional physiometric measurements using a different frequency of measurement as compared to the one or more initial physiometric measurements. Alternatively, the one or more instructions may further be configured to cause the wearable device to collect the one or more additional physiometric measurements using a revised set of one or more sensors of the wearable device. The revised set of one or more sensors may differ from the initial set of one or more sensors.

Further, the server may learn over time, for example by machine learning techniques, the sensor parameters that are sufficient and/or appropriate for providing an indication of circadian rhythms of the wearer of the device. For example, after analyzing an initial set of data and determining that the initial data is insufficient to characterize the circadian rhythm of the wearer, the server may generate one or more instructions configured to cause the wearable device to collect additional data. The server may then analyze the additional collected data to determine if the additional data is sufficient to characterize the circadian rhythm of the wearer. If the additional data is insufficient, the server will generate additional instructions configured to cause the wearable device to collect further additional data. This calibration process may proceed until the server has determined the optimal data collection parameters under which an indication of circadian rhythm can be determined. These optimal data collection parameters can include the combination of sensors, timing of data collection, and frequency of data collection, etc. The server may then update the collection algorithms of the wearable device by providing further instructions to the wearable device to continue to collect data according to the optimal data collection parameters.

Figure 5:
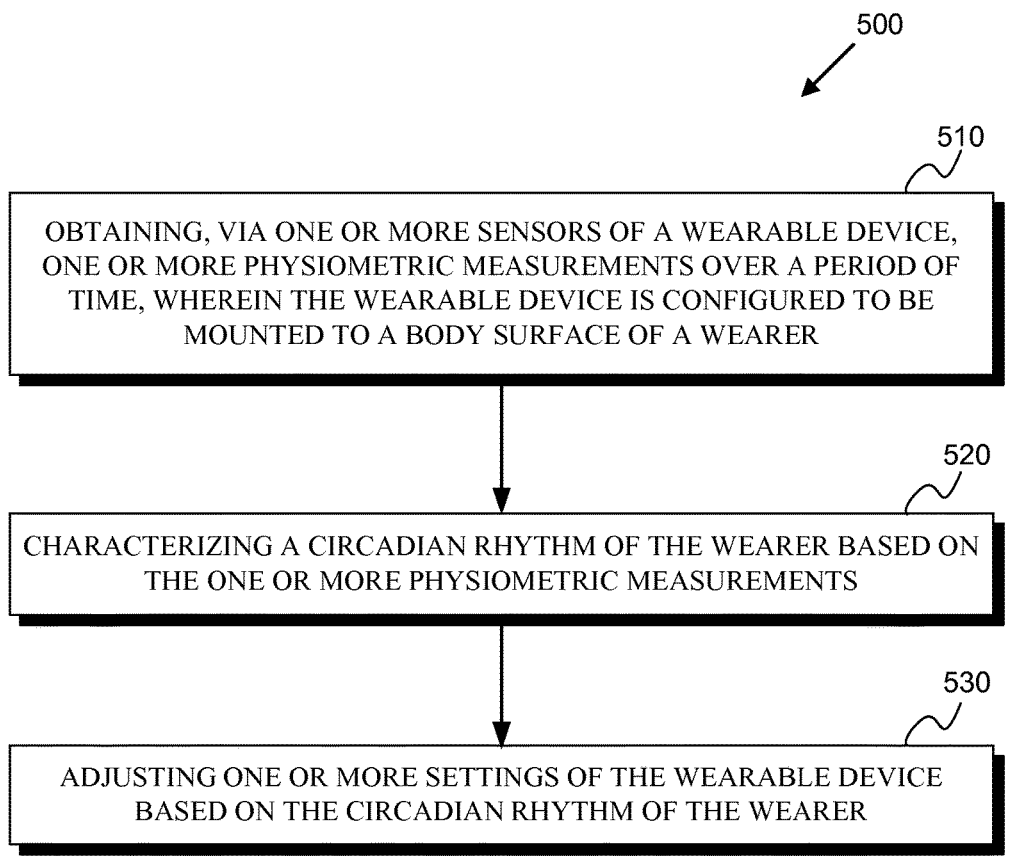
FIG. 5 is a flow chart of an example method, according to an example embodiment.

FIG. 5 is a flowchart of an example method 500 for detecting one or more circadian rhythms with a wearable device. The method may, for example, be carried out, at least in part, by a cloud computing device, such as server 140. One or more sensors on a wearable device obtain one or more physiometric measurements, such as measurements of body motions, measurements of pulse, measurements of blood oxygen saturation, measurements of blood pressure, or measurements of body temperature, over a period of time (510). The wearable device is configured to be mounted to a body surface of a wearer and may be provided as any of the wearable devices describe above, including wrist-mounted device 210. The one or more sensors may include any of the sensors, including sensors 230, described above. Based on the one or more physiometric measurements, a circadian rhythm of the wearer is characterized (520) by, for example, identifying one or more cyclical patterns in the one or more physiometric measurements. Based on the one or more cyclical patterns, one or more circadian rhythms, including sleeping, waking, eating, excretion and activity patterns may be identified.

One or more settings of the wearable device may then be adjusted based on the characterized circadian rhythm (530). For example, a timing of one or more actions performed by the wearable device may be adjusted based, at least in part, on the circadian rhythm. The one or more actions of the wearable device may include, for example, the time at which one or more sensors on the wearable device obtain physiometric data from the wearer, or the timing of providing alerts or recommendations to a wearer of the device.

While some examples discussed herein describe the server as generating the instructions for adjusting parameters of the one or more servers on the device, it is understood that the wearable device may include a processor sufficient to process the initial data and generate one or more instructions.

In some examples, the one or more identified circadian rhythms may be used to determine one or more metrics of a health state of the wearer of the device. A metric of health state may be based, at least in part, on a comparison of the one or more circadian rhythms with one or more typical circadian rhythms. These typical circadian rhythms may be patterns that are typical for the particular individual, or they may be circadian rhythms that are typical of a population of individuals, such as individuals having similar demographic data as the individual. For example, the server may identify a sleeping pattern of a wearer of the device and may compare that individual wearer's pattern to the sleeping patterns of other similar individuals. If the individual wearer's pattern is some degree different from the sleep pattern of the other similar individuals in the population, it may be determined that the wearer has an abnormal sleep pattern. In another example, the server may identify a pattern in the activity of an individual wearer over a period of time. The server may analyze the wearer's activity patterns and may identify a downward trend in the amount of body movement detected from that individual wearer over the period of time. Based on this, the server may identify a decline in the health state of the wearer.

Figure 6:
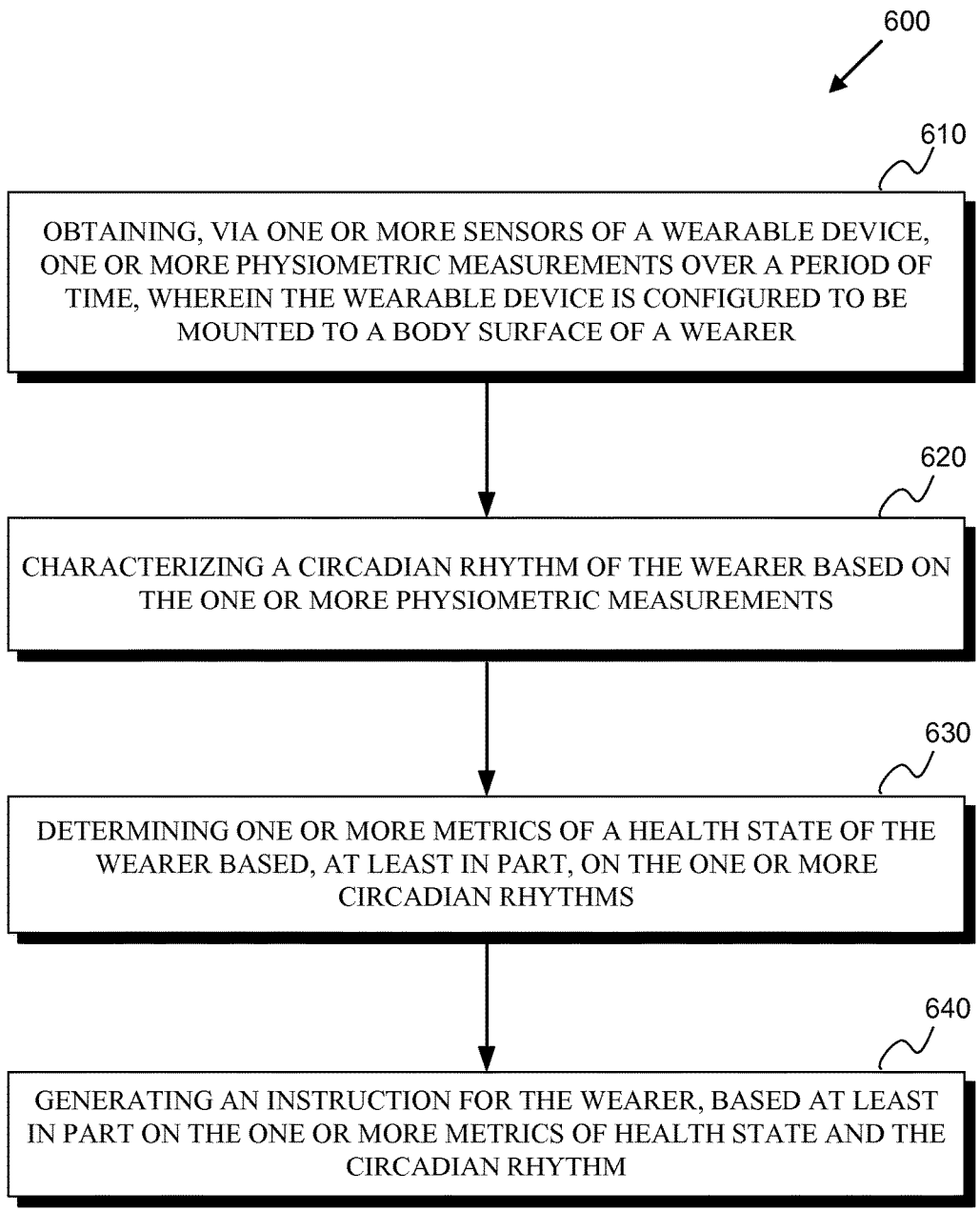
FIG. 6 is a flow chart of an example method, according to an example embodiment.

Further, the one or more circadian rhythms identified by the wearable device and/or server may be used to intervene on certain activities of the wearer. An example method 600 is illustrated in FIG. 6. One or more physiometric measurements are obtained via one or more sensors of a wearable device over a period of time. (610). The wearable device is configured to be mounted to a body surface of a wearer and may be provided as any of the wearable devices described above. Based on the one or more physiometric measurements, a circadian rhythm of the wearer is characterized. (620). One or more metrics of a health state of the wearer may also be determined based, at least in part, on the one or more circadian rhythms. (630). The one or more metrics of the wearer's health state may be determined based on a comparison of the circadian rhythm of the wearer with one or more typical circadian rhythms. These typical circadian rhythms may be circadian rhythms that are typical for a particular wearer, or typical for a population of wearers. The metrics of the wearer's health state may include any metrics of mental or physical health, metrics of a wearer's reaction to a particular therapeutic or drug regimen, metrics of a wearer's quality of sleep or physical or intellectual endurance.

An instruction for the wearer is generated based, at least in part, on the one or more metrics of health state and the circadian rhythm. The instruction may be any instruction for the wearer to adjust one or more activities, such as the dosage, type or timing of a therapeutic or drug regimen, a sleep-wake pattern, or the timing of physical or intellectual exertion. For example, it may be determined that a wearer as poor cardiac health and has been prescribed a particular pharmaceutical drug regimen intended to improve cardiac health. It may further be determined that, based on the wearer's cardiac rhythm, that the prescribed drug regimen is most efficacious if taken at 3:00 P. M. In this case, an instruction may be generated for the wearer to adjust the timing of administration of the drug to 3:00 P. M. In another example, the wearer may be instructed to adjust her sleep-wake times based on the characterized circadian rhythms. Other interventions in the wearer's daily activities are contemplated.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A method, comprising:
receiving, at a server, initial data from a wearable device, wherein the initial data comprises one or more initial physiometric measurements obtained by an initial set of one or more sensors of the wearable device over an initial period of time, wherein the wearable device is configured to be mounted to a body surface of a wearer;
determining, by the server, based on an analysis of the initial data, whether the initial data is insufficient to characterize a circadian rhythm of the wearer;
responsive to a determination that the initial data is insufficient to characterize a circadian rhythm of the wearer, transmitting, by the server, one or more instructions to the wearable device, wherein the one or more instructions are configured to cause the wearable device to collect additional data comprising one or more additional physiometric measurements over an additional period of time using a revised set of one or more sensors of the wearable device, wherein the revised set of one or more sensors differs from the initial set of one or more sensors.

2. The method of claim 1, wherein determining, based on an analysis of the initial data, whether the initial data is insufficient to characterize a circadian rhythm of the wearer comprises:
identifying at least one cyclical pattern in the initial data.

3. The method of claim 2, wherein determining, based on an analysis of the initial data, whether the initial data is insufficient to characterize a circadian rhythm of the wearer further comprises:
determining, by the server, whether one or more circadian rhythms of the wearer can be characterized based, at least in part, on the at least one cyclical pattern.

4. The method of claim 3, wherein the one or more circadian rhythms include at least one of a sleeping pattern, waking pattern, eating pattern, excretion pattern, or physical activity pattern.

5. The method of claim 1, wherein the one or more instructions are further configured to cause the wearable device to collect the one or more additional physiometric measurements using a different frequency of measurement as compared to the one or more initial physiometric measurements.

6. The method of claim 1, wherein the one or more physiometric measurements include at least one of measurements of body motions, measurements of pulse, measurements of blood oxygen saturation, measurements of blood pressure, or measurements of body temperature.

7. The method of claim 1, wherein the initial period of time is at least 24 hours.

8. A method, comprising:
obtaining, via one or more sensors of a wearable device, one or more initial physiometric measurements over a period of time, wherein the wearable device is configured to be mounted to a body surface of a wearer, and wherein the wearable device comprises a controller;
determining, based on an analysis of the one or more initial physiometric measurements, whether the one or more initial physiometric measurements are insufficient to characterize a circadian rhythm of the wearer;
responsive to determining that the one or more initial physiometric measurements are insufficient to characterize a circadian rhythm of the wearer, adjusting, by the controller, one or more settings of the one or more sensors such that one or more additional physiometric measurements obtained by the one or more sensors are sufficient to characterize a circadian rhythm, wherein the one or more settings specify at least one of a time of day at which the one or more sensors collect data, a frequency at which the one or more sensors collect data, or a type of data collected by the one or more sensors;

characterizing a circadian rhythm of the wearer based on the one or more additional physiometric measurements; and adjusting, by the controller, one or more settings of the wearable device based on the circadian rhythm of the wearer.

9. The method of claim 8, wherein characterizing a circadian rhythm of the wearer based on the one or more additional physiometric measurements comprises identifying one or more cyclical patterns in the one or more additional physiometric measurements.

10. The method of claim 9, wherein characterizing a circadian rhythm of the wearer based on the one or more additional physiometric measurements further comprises:

determining one or more circadian rhythms of the wearer based, at least in part, on the at least one cyclical pattern.

11. A wearable device, comprising:

a mount configured to mount the wearable device to a body surface;

one or more sensors, wherein the one or more sensors are configured to obtain one or more initial physiometric measurements; and a controller, wherein the controller is configured to:

determine, based on an analysis of the one or more initial physiometric measurements, whether the one or more initial physiometric measurements are insufficient to characterize a circadian rhythm of the wearer; and responsive to determining that the one or more initial physiometric measurements are insufficient to characterize a circadian rhythm of the wearer, adjust one or more settings of the one or more sensors such that one or more additional physiometric measurements obtained by the one or more sensors are sufficient to characterize a circadian rhythm, wherein the one or more settings specify at least one of a time of day at which the one or more sensors collect data, a frequency at which the one or more sensors collect data, or a type of data collected by the one or more sensors.

12. The wearable device of claim 11, wherein the controller comprises a processor configured to generate one or more instructions, wherein the instructions relate to the circadian rhythm.

13. The wearable device of claim 12, wherein the controller is configured to adjust one or more settings of the wearable device based on the one or more instructions.

14. The wearable device of claim 11, further comprising:

a wireless transceiver, wherein the controller is configured to control the wireless transceiver to transmit data to a server and to receive one or more instructions from the server, wherein the data comprises one or more physiometric measurements obtained by the one or more sensors over a period of time, and wherein the one or more instructions relate to the circadian rhythm.

15. The wearable device of claim 14, wherein the period of time is at least 24 hours.

16. A method, comprising:

sensing, via one or more sensors of a wearable device, one or more initial physiometric measurements over a period of time, wherein the wearable device is configured to be mounted to a body surface of a wearer, and wherein the wearable device comprises a controller;

determining, based on an analysis of the one or more initial physiometric measurements, whether the one or more initial physiometric measurements are insufficient to characterize a circadian rhythm of the wearer; and responsive to determining that the one or more initial physiometric measurements are insufficient to characterize a circadian rhythm of the wearer, adjusting, by the controller, one or more settings of the one or more sensors such that one or more additional physiometric measurements obtained by the one or more sensors are sufficient to characterize a circadian rhythm, wherein the one or more settings specify at least one of a time of day at which the one or more sensors collect data, a frequency at which the one or more sensors collect data, or a type of data collected by the one or more sensors;

characterizing a circadian rhythm of the wearer based on the one or more additional physiometric measurements;

determining one or more metrics of a health state of the wearer based, at least in part, on the one or more circadian rhythms; and generating an instruction for the wearer, based at least in part on the one or more metrics of health state and the circadian rhythm.

17. The method of claim 16, further comprising:

determining one or more metrics of a health state of the wearer of the device based, at least in part, on a comparison of the one or more circadian rhythms of the wearer with one or more typical circadian rhythms.

18. The method of claim 16, wherein the one or more instruction comprises an instruction for the wearer to adjust a therapeutic or pharmaceutical drug regimen.

19. The method of claim 16, wherein the one or more instruction comprises an instruction for the wearer to adjust a sleep-wake pattern.

20. The method of claim 10, wherein the one or more circadian rhythms include at least one of a sleeping pattern, waking pattern, eating pattern, excretion pattern, or physical activity pattern.

* * * * *